(12) United States Patent
Baba et al.

(10) Patent No.: US 8,038,621 B2
(45) Date of Patent: Oct. 18, 2011

(54) ULTRASONIC DIAGNOSTIC APPARATUS AND CATHETER TIP PART DETECTION METHOD

(75) Inventors: Tatsuro Baba, Otawara (JP); Hironobu Hongou, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 958 days.

(21) Appl. No.: 11/928,498

(22) Filed: Oct. 30, 2007

(65) Prior Publication Data

US 2008/0108901 A1 May 8, 2008

(30) Foreign Application Priority Data

Nov. 2, 2006 (JP) ................... 2006-298946

(51) Int. Cl.
*A61B 8/12* (2006.01)

(52) U.S. Cl. ........ 600/459; 600/462; 600/463; 600/466; 73/609; 324/635

(58) Field of Classification Search .......... 600/407–480; 73/623

See application file for complete search history.

(56) References Cited

U.S. PATENT DOCUMENTS

| | | | | |
|---|---|---|---|---|
| 3,492,564 A | * | 1/1970 | Baker, Jr. ................. | 324/329 |
| 5,867,800 A | * | 2/1999 | Leif .......................... | 701/23 |
| 5,966,016 A | * | 10/1999 | Suyama et al. .......... | 324/639 |
| 6,261,232 B1 | * | 7/2001 | Yokosawa et al. ....... | 600/443 |
| 6,266,552 B1 | * | 7/2001 | Slettenmark ............. | 600/424 |
| 6,622,560 B2 | * | 9/2003 | Song et al. ............... | 73/606 |
| 7,046,015 B2 | * | 5/2006 | Suginouchi et al. ...... | 324/635 |
| 2007/0055160 A1 | * | 3/2007 | Ng ............................ | 600/447 |

FOREIGN PATENT DOCUMENTS

| | | |
|---|---|---|
| JP | 4-129543 | 4/1992 |
| JP | 2002-315754 | 10/2002 |
| WO | WO2006/035199 | * 4/2006 |

OTHER PUBLICATIONS

Masanori Kunita, "Range Measurement in Ultrasound FMCW System" IEICE, vol. J88-A, No. 11, 2005, pp. 1297-1307.
Yoshimasa Daido, et al., "Range Measurement using Isosceles Sawtooth Modulation Signal in Ultrasound FMCW System", The Institute of Electronics, Information and Communication Engineers, IEICE Technical Report, EMCJ2005-95, MW2005-101, Oct. 2005, pp. 13-18 (With English Abstract).
U.S. Appl. No. 11/572,696, filed Jan. 25, 2007, Tetsuro Baba, et al.

* cited by examiner

*Primary Examiner* — Tse Chen
*Assistant Examiner* — Vani Gupta
(74) *Attorney, Agent, or Firm* — Oblon, Spivak, McClelland, Maier & Neustadt, L.L.P.

(57) ABSTRACT

An ultrasonic diagnostic apparatus includes plural ultrasonic transducers, a catheter signal detection unit and a position detection unit. The plural ultrasonic transducers are arrayed two-dimensionally for transmitting and receiving ultrasonic waves to and from an object. The catheter signal detection unit is configured to acquire a reception signal of a frequency modulated continuous wave from reception signals from at least three of the plural ultrasonic transducers. The frequency modulated continuous wave is transmitted from a catheter inserted in the object. The position detection unit is configured to detect a position of the catheter based on the acquired reception signal of the frequency modulated continuous wave.

24 Claims, 8 Drawing Sheets

ULTRASONIC DIAGNOSTIC APPARATUS AND CATHETER TIP PART DETECTION METHOD

BACKGROUND OF THE INVENTION

1. Field of the Invention

The present invention relates to an ultrasonic diagnostic apparatus and a catheter tip part detection method, and more particularly, to an ultrasonic diagnostic apparatus and a catheter tip part detection method which make it possible to detect a position coordinate of a tip part of a catheter, an ultrasonic probe having a thin diameter or the like inserted into a body of an object.

2. Description of the Related Art

The ultrasonic diagnostic apparatus performs ultrasonic transmission/reception in a plurality of directions in a patient body using an ultrasonic probe with a plurality of transducers arranged therein, and displays, on a monitor, ultrasonic image data generated based on reflected waves obtained during the ultrasonic transmission/reception. Because the ultrasonic diagnostic apparatus allows two-dimensional images or three-dimensional images in the body to be observed in real time by a simple operation of bringing an ultrasonic probe into contact with the body surface, it is extensively used for shape diagnosis or functional diagnosis of various organs.

Performing a treatment such as transcatheter arterial embolization (TAE), percutaneous transluminal coronary angioplasty (PTCA), percutaneous transluminal coronary recanalization (PTCR) or radiofrequency ablation (RFA), or various diagnoses, while ascertaining the position of the tip part of a catheter or a small-diameter ultrasonic probe inserted into a blood vessel or a digestive tract, or a puncture needle inserted into body tissues (hereinafter these are collectively referred to as a "catheter"), under the observation of real-time displayed ultrasonic image data, allows the accuracy and safety in an examination or treatment to be drastically improved. In addition, the diagnosis/treating method using ultrasonic image data has an advantage in being free of X-ray exposure compared with that using X-ray image data which has hitherto been executed for the same purpose.

However, when attempting to concurrently acquire information on the body tissues and information on the catheter tip part using the ultrasonic probe arranged on the body surface of an object, it has been difficult to make a constant observation of the catheter tip part, on the ultrasonic image data, because ultrasonic waves radiated from the transducers in the ultrasonic probe make specular reflections (mirror reflections) on the smooth surface of the catheter.

Specifically, since a diameter of a general catheter is about 2-3 mm, it is impossible to observe a general catheter on an ultrasonic image with enough accuracy though the catheter can be observed to a certain extent. Particularly, when an RITA (radio frequency interstitial tissue ablation) needle is attached with a catheter for RFA, it is impossible to observe the RITA needle on an ultrasonic image absolutely since the diameter of the RITA needle is not over 1 mm.

In order to solve such a problem, a method has been proposed wherein a minute transducer for receiving ultrasonic waves is mounted on the catheter tip part, and ultrasonic waves radiated from transducers in the ultrasonic probe arranged on the body surface of the object are received using the transducer at the catheter tip part to thereby detect the tip position thereof (see, for example, Japanese Patent Application (Laid-Open) No. 4-129543).

Another method has also been proposed wherein ultrasonic waves radiated from the transducer mounted on the catheter tip part are received by each of three discrete transducers in the ultrasonic probe arranged on the body surface of the object, and the tip position of the catheter is detected based on delayed times between the three obtained reception signals (see, for example, Japanese Patent Application (Laid-Open) No. 2002-315754). According to this method, a display of position information on the catheter tip part can be superimposed on a display of three-dimensional image data on blood vessels or the like acquired by the ultrasonic probe, or a display of endoscopic image data as seen from the viewpoint of the catheter tip part (so-called fly-through image data) can be achieved.

By the above-described methods which are described on Japanese Patent Application (Laid-Open) No. 4-129543 and Japanese Patent Application (Laid-Open) No. 2002-315754, the catheter tip part can be detected independent of the material and the shape of the catheter, and the incident angle of ultrasonic waves radiated from the transducers in the ultrasonic probe.

However, in these methods, broadband ultrasonic pulses radiated from the transducer mounted on the catheter tip part or the transducers in the ultrasonic probe arranged on the body surface are received by the transducers in the ultrasonic probe or the transducer mounted on the catheter tip part, and arrival times (delayed times) of the obtained pulses are measured to thereby detect the position of the catheter tip part. Therefore, if a non-negligible ultrasonic attenuation occurs in the body tissues intervening between the ultrasonic probe and the catheter, the reception sensitivity of ultrasonic pulses in the transducers in the ultrasonic probe or the transducer at the catheter tip part is deteriorated, and also, in the above-described ultrasonic pulses having a broadband frequency spectrum, the higher the frequency of a pulse component, the larger becomes the attenuation that the component undergoes. As a result, the waveforms of the ultrasonic pulses are significantly deformed, thereby making it difficult to accurately measure the arrival times of the ultrasonic pulses.

Furthermore, according to the above-described methods which are described on Japanese Patent Application (Laid-Open) No. 4-129543 and Japanese Patent Application (Laid-Open) No. 2002-315754, when sound speeds of ultrasonic waves in body tissues are uneven, it is undesirably difficult to accurately detect the position of the catheter tip part even if the above-described arrival times are accurately measured, because the arrival times of ultrasonic pulses depend on positions of transducers in the ultrasonic probe or body tissues.

SUMMARY OF THE INVENTION

The present invention has been made in light of the conventional situations, and it is an object of the present invention to provide an ultrasonic diagnostic apparatus and a catheter tip part detection method which make it possible to detect a position coordinate of a tip part of a catheter or the like inserted in a body of an object and display tip part position information precisely without adverse effect due to attenuation of an ultrasonic wave by tissue of a living body, nonuniformity of the sonic velocity or the like when the tip part position information is to be displayed with overlapping the information on ultrasonic image data.

The present invention provides an ultrasonic diagnostic apparatus comprising: plural ultrasonic transducers arrayed two-dimensionally for transmitting and receiving ultrasonic waves to and from an object; a catheter signal detection unit configured to acquire a reception signal of a frequency modulated continuous wave from reception signals from at least three of said plural ultrasonic transducers, the frequency modulated continuous wave being transmitted from a catheter inserted in the object; and a position detection unit configured to detect a position of the catheter based on the acquired reception signal of the frequency modulated continuous wave, in an aspect to achieve the object.

The present invention also provides a catheter tip part detection method comprising: acquiring a reception signal of a frequency modulated continuous wave from reception signals from at least three of two-dimensionally arrayed plural ultrasonic transducers, the frequency modulated continuous wave being transmitted from a catheter inserted in an object; and detecting a position of the catheter based on the acquired reception signal of the frequency modulated continuous wave, in an aspect to achieve the object.

According to the present invention as described above, it becomes possible to detect a position coordinate of a tip part of a catheter or the like inserted in a body and display tip part position information precisely without adverse effect due to attenuation of an ultrasonic wave by tissue of a living body, nonuniformity of the sonic velocity or the like when the tip part position information is to be displayed with overlapping the information on ultrasonic image data. Consequently, accuracy and safety on diagnosis and cure using a catheter are improved significantly.

DESCRIPTION OF THE PREFERRED EMBODIMENTS

An embodiment according to the present invention will be described below with reference to the drawings.

According to the embodiment of the present invention described below, a linear Frequency Modulated (chirp modulated) Continuous Wave (hereinafter called FMCW) of which center is set to the first frequency f1 is generated at a desired period Tm firstly, and subsequently a minute transducer loaded to tip part of a catheter inserted in a body of an object is driven by an FMCW drive signal generated based on the FMCW to radiate the first ultrasonic wave. Then, the first ultrasonic wave radiated from the transducer on the catheter tip part is received by plural transducers selected from transducers two-dimensionally-arrayed in an ultrasonic probe arranged on the body surface of the object, and subsequently a frequency of difference (beat frequency) is detected by multiplication processing between the reception signal and the FMCW described above. Further, a distance between the transducer on the catheter tip part and each of the plural transducers of the ultrasonic probe is calculated based on the beat frequency, and subsequently a relative position coordinate of the catheter tip part to the ultrasonic probe is detected based on these distances.

On the other hand, an ultrasonic pulse (the second ultrasonic wave) of which center frequency is the second frequency f2 is transmitted to and received from three-dimensional region, where the catheter tip part is positioned, of the object using two-dimensionally arrayed transducers by the ultrasonic probe, and subsequently three dimensional image data is generated based on volume data obtained by transmission and reception of the second ultrasonic wave. Then, the positional information of the catheter tip part is overlapped on the obtained three-dimensional image data to be displayed on a display unit.

Incidentally, in the embodiment of the present invention described below, a case where volume rendering image data serving as three-dimensional image data is generated based on B mode data will be described. However, volume rendering image data based on other ultrasonic data such as color Doppler data may be generated. Further, other three-dimensional image data such as surface rendering image data instead of volume rendering image data may be generated.

(Configuration of Apparatus)

Figure 1:
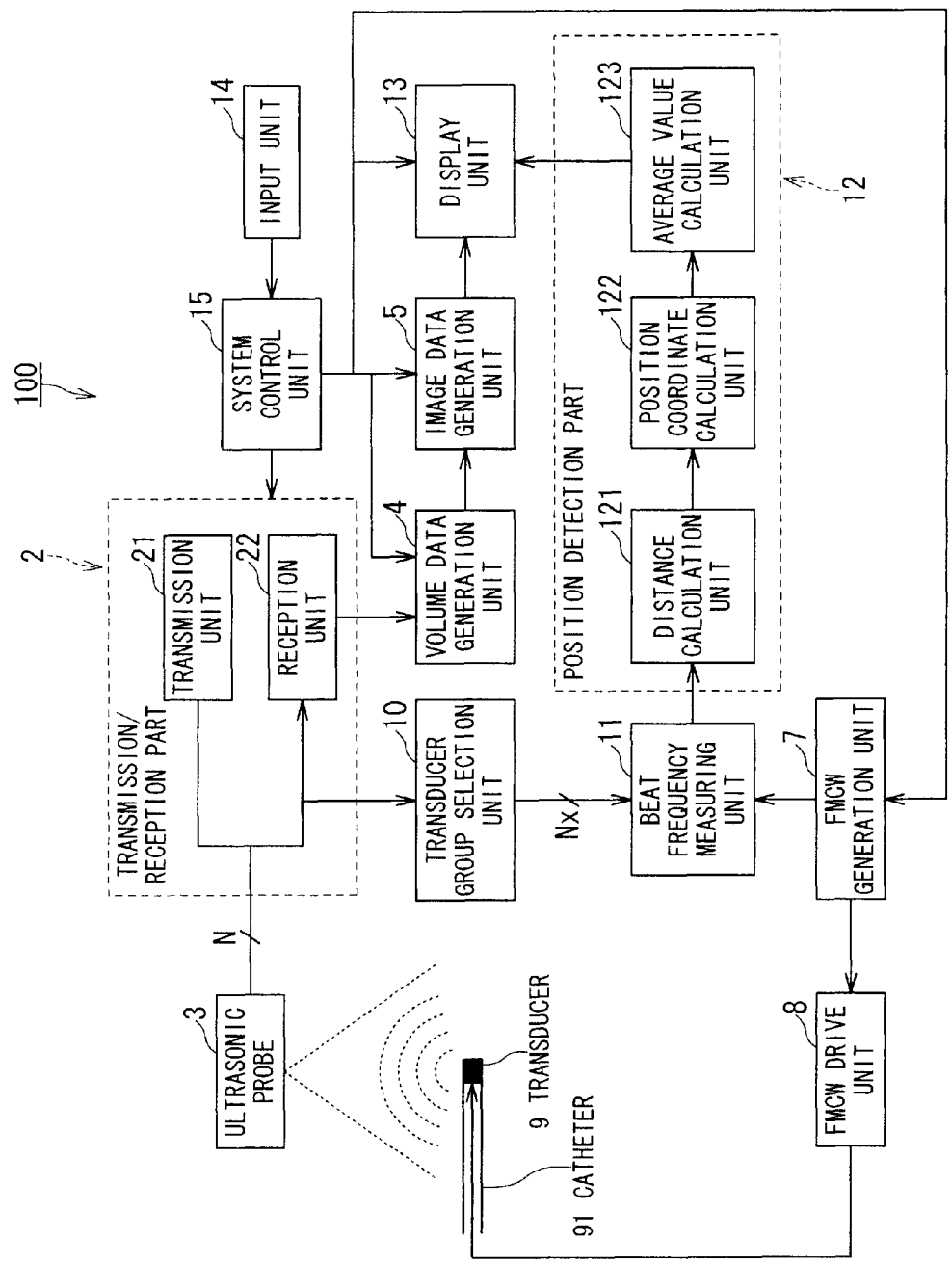
FIG. 1 is a block diagram showing a whole configuration of an ultrasonic diagnostic apparatus according to an embodiment of the present invention.
Figure 2:
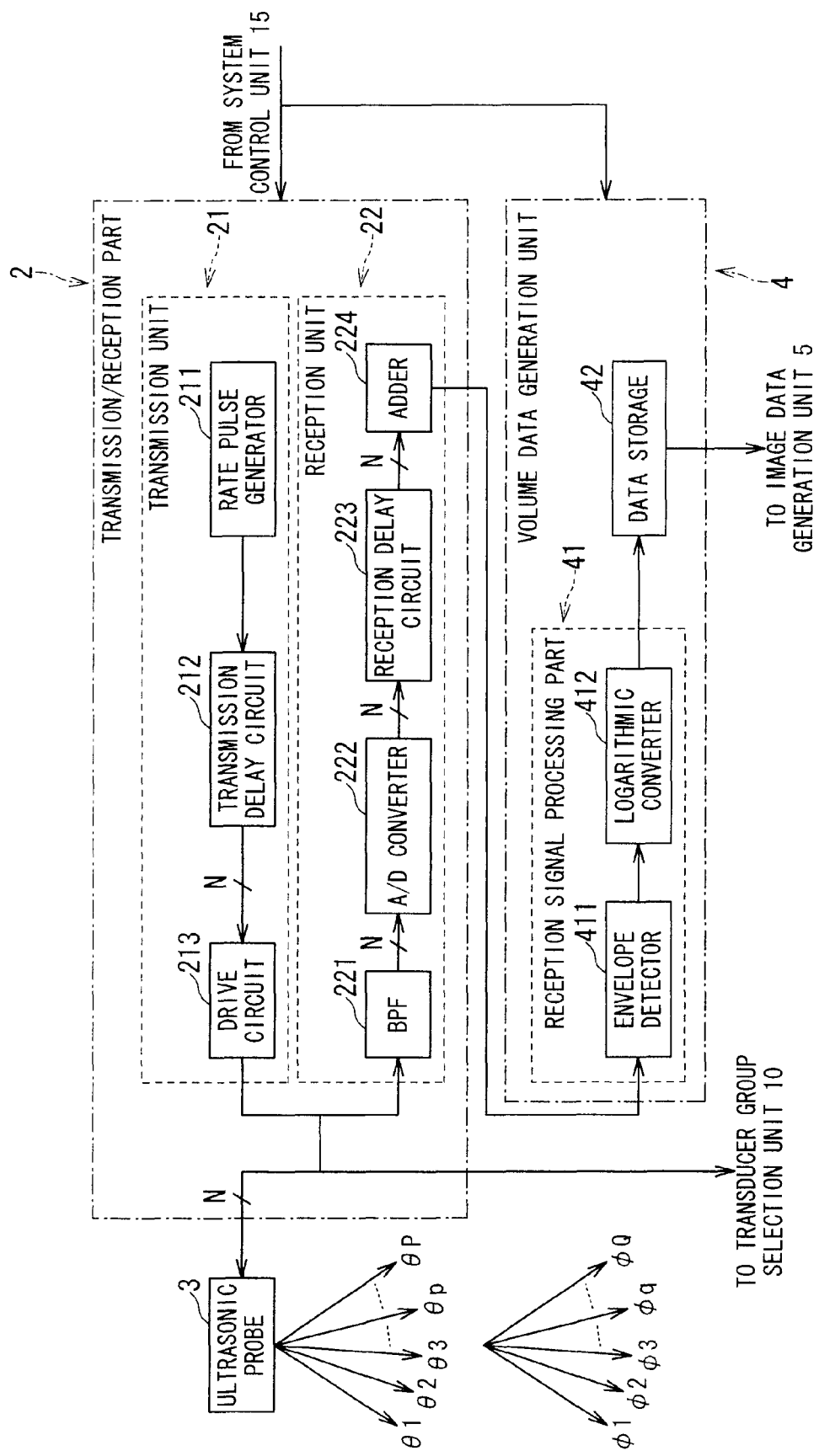
FIG. 2 is a block diagram showing a configuration of the transmission/reception part and the volume data generation unit included in the ultrasonic diagnostic apparatus according to the embodiment.
Figure 3:
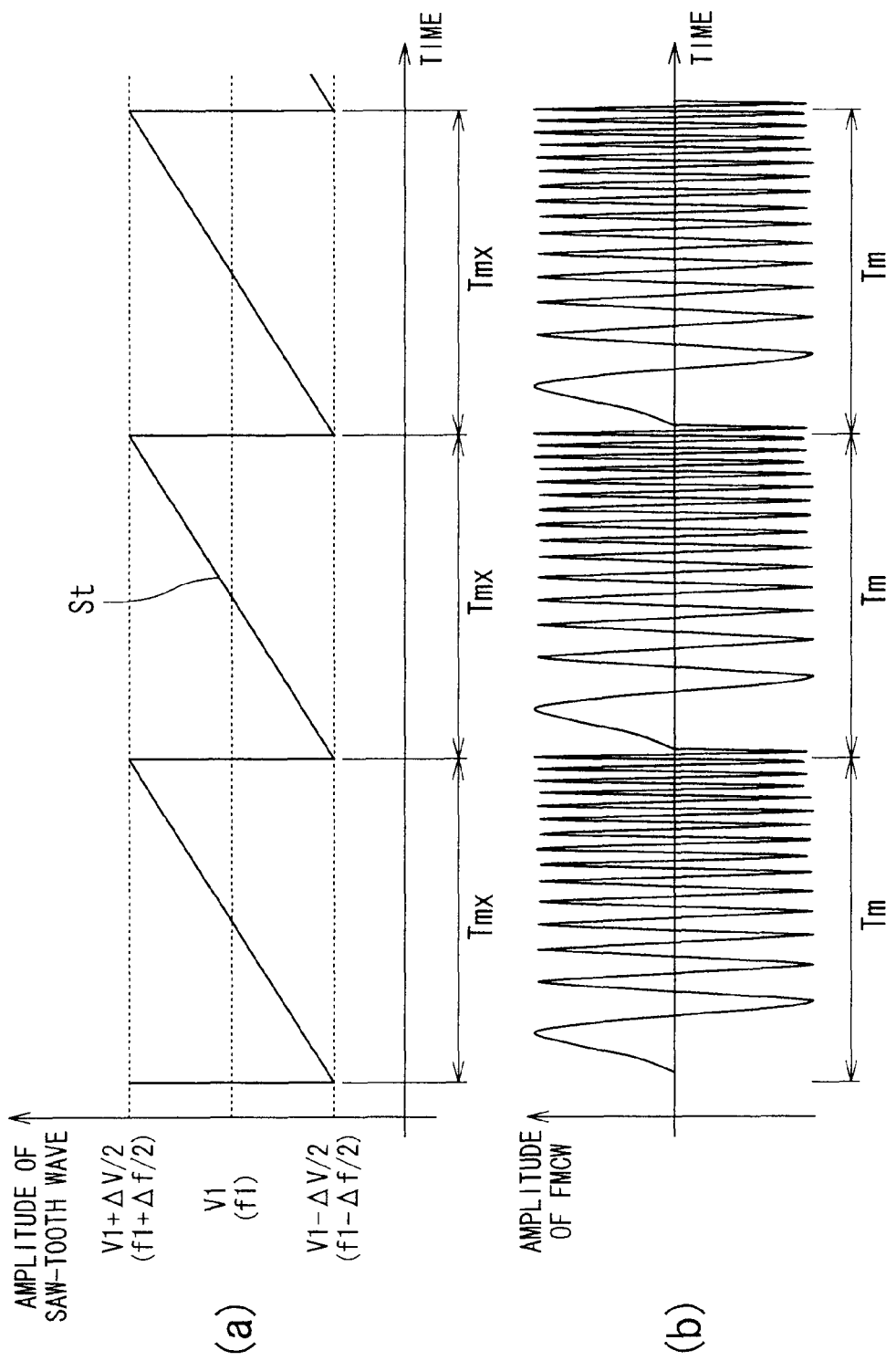
FIG. 3 is a diagram explaining an FMCW generated by the FMCW generation unit of the embodiment.
Figure 4:
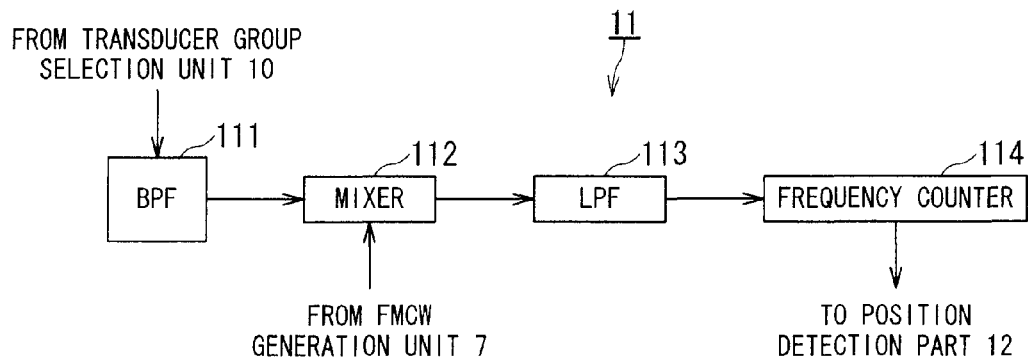
FIG. 4 is a block diagram showing a configuration of the beat frequency measuring unit included in the ultrasonic diagnostic apparatus according to the embodiment.

A configuration of an ultrasonic diagnostic apparatus according to the present embodiment will be described with reference to FIGS. 1 to 7. FIG. 1 is a block diagram showing a whole configuration of the ultrasonic diagnostic apparatus. FIG. 2 is a block diagram of a transmission/reception part and a volume data generation unit included in the ultrasonic diagnostic apparatus. FIG. 4 is a block diagram showing a concrete configuration of a beat frequency measuring unit included in the ultrasonic diagnostic apparatus.

The ultrasonic diagnostic apparatus 100 in this embodiment shown in FIG. 1 includes an ultrasonic probe 3 having a plurality of transducers transmitting ultrasonic pulses (second ultrasonic waves) into a three-dimensional region in the object body with a catheter 91 inserted therein, receiving the second ultrasonic waves reflected on the body tissues and first ultrasonic wave radiated by a transducer 9 (to be described later) mounted on the tip part of the catheter 91, and converting them into electric signals (reception signals); a transmission/reception part 2 that supplies the plurality of transducers in the ultrasonic probe 3 with drive signals for radiating the second ultrasonic waves in a predetermined direction in the object and that performs phasing/adding of the reception signals from a plurality of channels based on the second ultrasonic waves, received from the predetermined direction by these transducers; a volume data generation unit 4 that signal-processes the reception signals after the phasing/adding to thereby generate B-mode data, and that stores the B-mode data obtained while successively renewing the transmission/reception direction of ultrasonic waves, relating to the transmission/reception direction, to thereby generate volume data; and an image data generation unit 5 that generates three-dimensional image data by rendering processing the above-described volume data.

The ultrasonic diagnostic apparatus 100 further includes an FMCW generation unit 7 that generates an FMCW that is linearly frequency-modulated at a predetermined period; an FMCW drive unit 8 that amplifies the FMCW into a predetermined amplitude to generate a drive signal (FMCW drive signal), to thereby drive the transducer 9 mounted on the tip part of the catheter 91; a transducer 9 that is mounted on the tip part of the catheter 91 inserted into the object body and that radiates the first ultrasonic wave in a substantially omnidirectional manner under the drive by an FMCW drive signal; a transducer group selection unit 10 that, in order to detect position coordinates of the transducer 9, selects a plurality of transducer groups in which three transducers are grouped into one transducer group, from among a plurality of transducers in the ultrasonic probe 3; a beat frequency measuring unit 11 that multiplies the reception signal based on the first ultrasonic wave, obtained by each of the three transducers in each of the selected transducer groups, by an FMCW generated by the FMCW generation unit 7, to thereby measure a beat frequency; a position detection part 12 that, based on this beat frequency, calculates the distance between each of the three transducers in each of the transducer groups and the transducer 9 at the catheter tip part to thereby to detect position coordinates of the catheter tip part with respect to each of the transducer groups, and that, by applying an averaging process to these position coordinates, detects relative position coordinates of the catheter tip part with respect to the ultrasonic probe 3; a display unit 13 that displays, in a superimposed manner, the position information (marker) on the catheter tip part based on the position coordinates on a display of the three-dimensional image data generated by the image data generation unit 5; an input unit 14 that performs an input of information on the object or a setting of three-dimensional image data generation conditions; and a system control unit 15 that exerts general control over the above-described units in the ultrasonic diagnostic apparatus 100.

The ultrasonic probe 3 transmits/receives ultrasonic pulses (second ultrasonic waves) with a center frequency f2 into a three-dimensional region in the body by bringing its front end part having N transducers (not shown) two-dimensionally arranged, into contact with the body surface, and further receives an ultrasonic FMCW (first ultrasonic wave) with a center frequency f1, radiated from the transducer 9 mounted on the tip part of the catheter 91. The N transducers are electro-acoustic converters. During transmission, the N transducers each have a function of converting an electric pulse (a drive pulse) into an ultrasonic wave pulse (transmission ultrasonic wave), and during reception, they each have a function of converting a reception ultrasonic wave into an electric reception signal. Each of the N transducers is connected to the transmission/reception part 2 through an N channel multicore cable (not shown). Here, the ultrasonic probe 3 includes a type adaptable to a sector scan, a type adaptable to a linear scan, and a type adaptable to a convex scan. In this embodiment, the description is made of the case where an ultrasonic probe for the sector scan is used, but an ultrasonic probe adaptable to the linear scan or the convex scan may also be used.

Next, the transmission/reception part 2 shown in FIG. 2 includes a transmission unit 21 that supplies the drive signals for radiating the second ultrasonic waves to the N transducers in the ultrasonic probe 3; and a reception unit 22 that performs phasing/adding of N channel reception signals based on the second ultrasonic waves, reflecting on the body tissues and received by the above-described transducers.

The transmission unit 21 includes a rate pulse generator 211 that generates a rate pulse determining a transmission repetition period of the second ultrasonic waves; a transmission delay circuit 212 that, during transmission, provides the rate pulse with a delayed time for converging the second ultrasonic waves to a predetermined depth and a delayed time for transmitting them in a predetermined direction, and a drive circuit 213 that, based on the delayed times of the rate pulse, generates a drive pulse to drive each of the N transducers incorporated in the ultrasonic probe 3.

The reception unit 22 includes a band-pass filter (BPF) 221 that eliminates reception signal component due to the first ultrasonic wave having the center frequency f1, from the N channel reception signals supplied from the transducers in the ultrasonic probe 3, to extracts reception signal component due to the second ultrasonic waves each having a center frequency f2 (f2>f1); an A/D (analog-to-digital) converter 222 that A/D converts N channel reception signals based on the second ultrasonic waves; a reception delay circuit 223 that provides each of the A/D converted reception signals with a delayed time for converging the second ultrasonic waves received from the predetermined depth and a delayed time for setting a reception directivity with respect to the second ultrasonic waves; and an adder 224 that adds and combines the reception signals outputted from the reception delay circuit 223. The reception delay circuit 223 and the adder 224 perform phasing/adding of the N channel reception signals due to the second ultrasonic waves, obtained from a predetermined direction of the object.

The volume data generation unit 4 includes a reception signal processing part 41 that signal-processes the reception signals due to the second ultrasonic waves after phasing/adding, outputted from the reception unit 22 in the transmission/reception part 2, to thereby generate B-mode data; a data storage 42 that successively stores the B-mode data relating to the transmission/reception direction of ultrasonic waves to generate volume data in a three-dimensional region in the object. Here, the above-described reception signal processing part 41 includes an envelope detector 411 that envelope-detects the reception signals supplied from the adder 224 in the reception unit 22; and a logarithmic converter 412 that converts the amplitudes of the reception signals that have been envelope-detected into logarithms to generate B-mode data. Meanwhile, the reception signal processing part 41 may be configured to reverse the order of the envelope detector 411 and the logarithmic converter 412.

Next, the image data generation unit 5 has a function of rendering processing volume data generated by the volume data generation unit 4 to generate three-dimensional image data. For example, the image data generation unit 5 includes an opacity/tone setting unit and a rendering processing unit (neither of which is shown). The opacity/tone setting unit sets, in units of voxel, an opacity or a tone based on voxel values of the volume data read from the data storage 42 in the volume data generation unit 4. On the other hand, the rendering processing unit rendering processes the volume data, based on information on the opacity or the tone set by the opacity/tone setting unit to generate three-dimensional image data. Here, specific methods for the rendering processing are omitted from detailed description since they are described on above-mentioned Japanese Patent Application (Laid-Open) No. 2002-315754.

The FMCW generation unit 7 has, for example, a voltage controlled oscillator (VCO) circuit and a saw-tooth wave generation circuit (each not shown). The saw-tooth wave generation circuit generates a saw-tooth wave based on a repetition period Tm in frequency modulation, frequency shift width Δf in frequency modulation, and the center frequency f1 of the FMCW that are each supplied from the system control unit 15. The VCO circuit generates an FMCW of which the frequency continuously changes at the period Tm based on the saw-tooth wave. FIG. 3(a) shows a saw-tooth wave St generated by the saw-tooth wave generation circuit, and FIG. 3(b) shows an FMCW generated by the VCO circuit based on the saw-tooth wave St. As shown in FIG. 3, the repetition period Tm for frequency modulation in the FMCW is determined by the period Tmx (Tmx=Tm) of the saw-tooth wave St, and the center frequency f1, the maximum frequency (f1+Δf/2), and the minimum frequency (f1−Δf/2) of the FMCW, respectively, are determined by the average amplitude V1, the maximum amplitude (V1+ΔV/2), and the minimum amplitude (V1−ΔV/2) of the saw-tooth wave St.

Here, the above-described frequency components (f1−Δf/2) to (f1+Δf/2) included in the FMCW are set in bandwidths such as not to overlap the frequency components of the second ultrasonic waves used for the generation of three-dimensional image data. For example, when the center frequency f2 of the second ultrasonic wave is 2.2 MHz and the bandwidth BW2 thereof is 2.4 MHz, the center frequency f1 of the FMCW is set to 0.8 MHz and the bandwidth BW1 (BW1≈Δf) thereof is set to 0.2 MHz.

Referring back to FIG. 1, the FMCW drive unit 8 has an amplifier circuit (not shown), which amplifies the FMCW supplied from the FMCW generation unit 7 into a predetermined amplitude to generate an FMCW drive signal, and which drives the transducer 9 mounted on the tip part of the catheter 91 to radiate the first ultrasonic wave. The transducer 9 is a minute electro-acoustic conversion element having substantially the same resonant frequency as the center frequency f1 of the FMCW. Because the aperture of the transducer 9 mounted on the tip part of the catheter 91, having an outer diameter of about 1 mm is smaller than the wavelength of the first ultrasonic wave having a center frequency of 0.8 MHz, the radiation characteristic of the first ultrasonic wave radiated from the transducer 9 driven by the FMCW drive signal is substantially omnidirectional.

In order to detect the position coordinates of the transducer 9 (i.e., the position coordinates of the catheter tip part), the transducer group selection unit 10 selects transducers to receive the first ultrasonic wave radiated by this transducer 9, from among a plurality of transducers two-dimensionally arranged in the ultrasonic probe 3. In this case, the transducer groups is selected in which three discrete transducers that do not exist on the same straight line are grouped into one transducer group. For example, when the position coordinates of the transducer 9 are detected using J transducer groups Na1 to NaJ, the transducer group selection unit 10 selects Nx (Nx=3J) pieces, in total, of transducers Qij (i=1 to 3, j=1 to J), from among the transducers two-dimensionally arranged in the ultrasonic probe 3. However, mutually different transducer groups may be constituted using a common transducer.

The position coordinates of the catheter tip part with the transducer 9 mounted thereon can be detected by one transducer group (e.g., the transducer group Na1 constituted of transducers Q11, Q21, and Q31). However, in this embodiment, by using a plurality of transducer groups Na1 to Naj, the relative position coordinates of the catheter tip part with respect to each of these transducer groups are detected, and the J sets of position coordinates obtained are subjected to averaging processing or statistical processing, whereby the relative position coordinates of the catheter tip part with respect to the ultrasonic probe 3 is detected with high accuracy.

The selection of the transducer groups Na1 to NaJ by the transducer group selection unit 10 is performed in actuality by selecting reception signals in Nx (3J) pieces, in total, of channels, received by the transducers Qij (i=1 to 3, j=1 to J), from among N channel reception signals that are supplied from each of the transducers of the ultrasonic probe 3 to the reception unit 22 in the transmission/reception part 2. Herein, the above-described reception signals selected include reception signal component due to the second ultrasonic waves, radiated from the transducers in the ultrasonic probe 3 and reflected on the body tissues; and reception signal component due to the first ultrasonic wave, directly propagating from the transducer 9 at the catheter tip part through the body tissues.

Next, the configuration and operations of the beat frequency measuring unit 11 will be described with reference to the block diagram in FIG. 4. The beat frequency measuring unit 11 includes a band-pass filter (BPF) 111, a mixer 112, a low-pass filter (LPF) 113, and a frequency counter 114.

Figure 5:
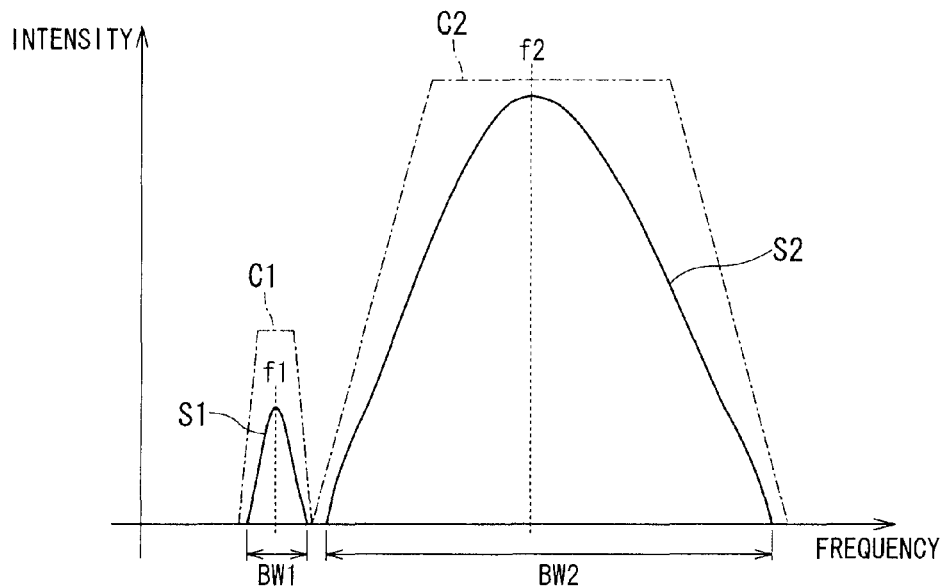
FIG. 5 is a diagram showing a frequency spectrum of a reception signal acquired by the ultrasonic probe according to the embodiment.

The BPF 111 eliminates the reception signal component due to the second ultrasonic waves, out of the reception signals obtained from the transducers of the ultrasonic probe 3, having been selected by the transducer group selection unit 10, to extract only the reception signal component due to the first ultrasonic wave. FIG. 5 shows a frequency spectrum of reception signals obtained from the transducers in the ultrasonic probe 3. This frequency spectrum includes reception signal component S1 due to the first ultrasonic wave and reception signal component S2 due to the second ultrasonic waves.

Specifically, the above-described frequency spectrum is constituted of a frequency spectrum S1 of the first ultrasonic wave having a center frequency f1 (f1=0.8 MHz) and a bandwidth BW1 (BW1=0.2 MHz), and a frequency spectrum S2 of the second ultrasonic wave having a center frequency f2 (f2=2.2 MHz) and a bandwidth BW2 (BW2=2.4 MHz). By the BPF 111 of the beat frequency measuring unit 11, having a filter pass characteristic shown by a chain line C1 in FIG. 5, only the reception signal component S1 due to the first ultrasonic wave is extracted from each of the reception signals supplied by the transducer group selection unit 10. On the other hand, a chain line C2 in FIG. 5 shows a filter pass characteristic of the BPF 221 provided in the reception unit 22 for eliminating the reception signal component S1 due to the first ultrasonic wave, out of reception signals obtained from the transducers in the ultrasonic probe 3, and for extracting only the reception signal component due to the second ultrasonic waves.

Next, the mixer 112 shown in FIG. 4 multiplies the reception signal component S1 due to the first ultrasonic wave, outputted from the BPF 111 by the FMCW supplied from the FMCW generation unit 7, and generates a reception signal having a sum frequency and a reception signal having a difference frequency (beat frequency). The low-pass filter (LPF) 113 applies a filtering process to reception signals outputted by the mixer 112 to detect reception signals with a beat frequency. The frequency counter 114 is constituted, e.g., of a zero-cross counter, and measures the beat frequency of reception signals supplied from the LPF 113 in a predetermined time period.

Returning now to FIG. 1, the position detection part 12 includes a distance calculation unit 121 that, based on the beat frequency measured by the frequency counter 114, calculates distances R1j, R2j, and R3j (j=1 to J) between three transducers Q1j, Q2j, and Q3j (j=1 to J) in each of the transducer groups Naj (j=1 to J) selected in the transducer group selection unit 10 and the transducer 9 mounted on the tip part of the catheter 91; a position coordinate calculation unit 122 that, based on the obtained distances R1j, R2j, and R3j (j=1 to J), detects relative position coordinates (xo(j), yo(j), zo(j)) (j=1 to J) of the catheter tip part with respect to each of the transducer groups Naj (j=1 to J); and an average value calculation unit 123 that calculates the relative position coordinates (x, y, z) of the catheter tip part with respect to the ultrasonic probe 3 by adding and averaging the position coordinates (xo(j), yo(j), zo(j)) (j=1 to J) with respect to the transducer groups Naj (j=1 to J).

Figure 6:
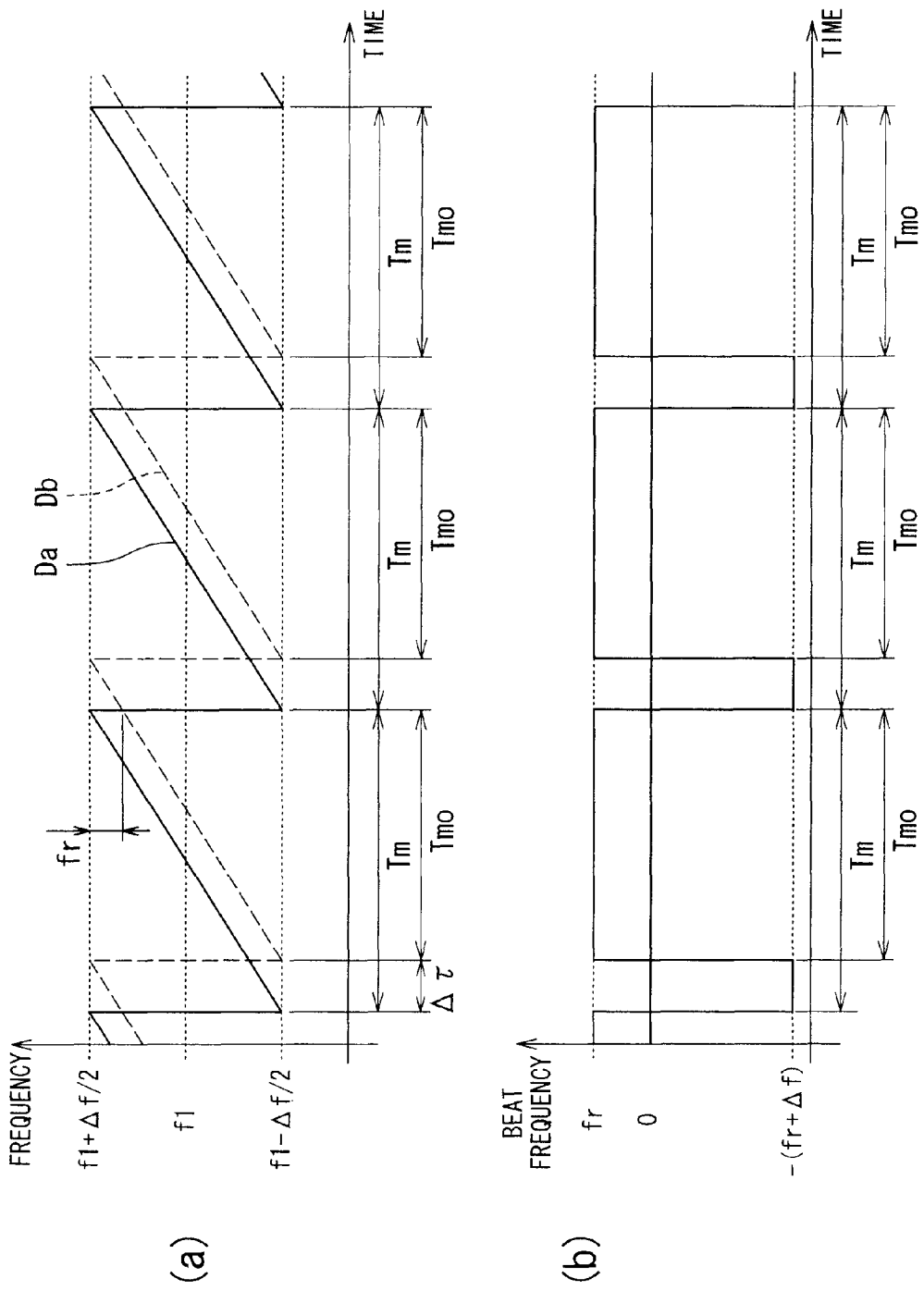
FIG. 6 is a diagram explaining a method for measuring a beat frequency by the beat frequency measuring unit according to the embodiment.

Next, a method for measuring the beat frequency by the above-described beat frequency measuring unit 11 will be now described in more detail with reference to FIG. 6. FIG. 6 is a diagram explaining operations of the beat frequency measuring unit 11. Solid line Da in FIG. 6(a) indicates a frequency of FMCW inputted into the mixer 112 in the beat frequency measuring unit 11 from the FMCW generation unit 7. Dotted line Db in FIG. 6(a) indicates a frequency of reception signal due to the first ultrasonic wave, the reception signal being received by a transducer in the ultrasonic probe 3, distant from the catheter tip part by a distance R to be described later, and being inputted into the mixer 112 via the BPF 111 in the beat frequency measuring unit 11. On the other hand, FIG. 6(b) shows the beat frequency of the reception signal outputted from the mixer 112 at this time.

In this case, the time $\Delta\tau$ required until the first ultrasonic wave radiated from the transducer 9 at the catheter tip part is received by a transducer in the ultrasonic probe 3 is represented by $\Delta\tau=R/C$, where the distance between the transducer 9 at the catheter tip part and the transducer in the ultrasonic probe 3 is denoted by R, and the sound speed in the body is denoted by C. That is, as shown in FIG. 6(a), the above-described reception signal inputted into the mixer 112 via the BPF 111 is delayed by $\Delta\tau$ with respect to an FMCW inputted from the FMCW generation unit 7. The frequency fr of the FMCW that changes during $\Delta\tau$ can be expressed by the following expression (1).

$$fr = \frac{\Delta f}{Tm}\Delta\tau = \frac{R\Delta f}{TmC} \quad (1)$$

Therefore, by multiplying the reception signal in the mixer 112 by the FMCW, a reception signal having a difference frequency of the reception signal and the FMCW (beat frequency) fr is generated together with a reception signal having a sum frequency thereof, in a time period Tmo in FIG. 6(b). Then, the LPF 113 applies a filtering process to the reception signals outputted from the mixer 112 to extract only the reception signal with the beat frequency fr. The frequency counter 114 measures the beat frequency fr of the reception signal, e.g., by the zero-cross method.

Next, the distance calculation unit 121 in the position detection part 12 calculates the distance R between the transducer 9 at the catheter tip part and the transducer in the ultrasonic probe 3, by substituting the beat frequency fr measured in the beat frequency measuring unit 11 into the following expression (2) obtained by deforming the above-described expression (1).

$$R = \frac{frTmC}{\Delta f} \quad (2)$$

Figure 7:
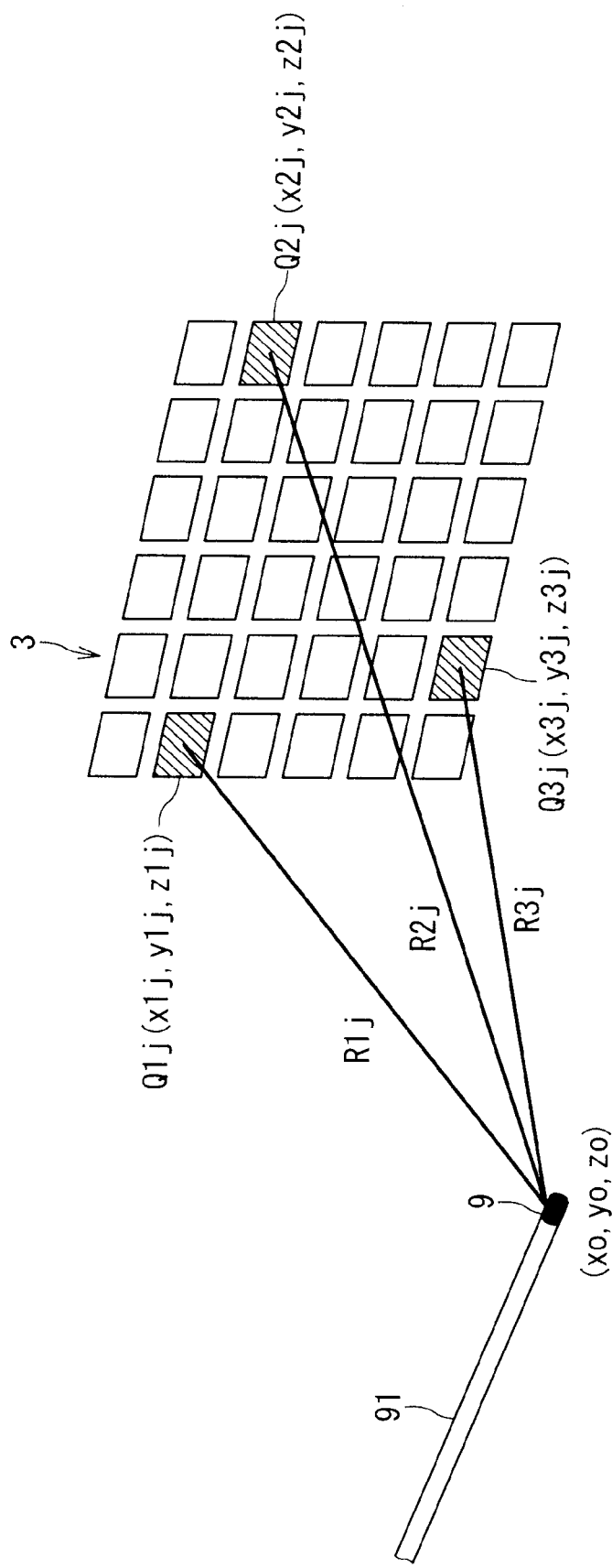
FIG. 7 is a diagram explaining a method for calculating a position coordinate of a tip part of a catheter by the position coordinate calculation unit according to the embodiment.

A method for calculating the position coordinates of the catheter tip part by the position coordinate calculation unit 122 in the position detection part 12 will be now described with reference to FIG. 7. Here, FIG. 7 is illustrated regarding the case where, using transducer groups Naj arbitrarily selected by the transducer group selection unit 10 from among the transducers two-dimensionally arranged in the ultrasonic probe 3, relative position coordinates (xo, yo, zo) of the catheter tip part with respect to the transducer groups Naj are detected. Here, the transducer group Naj are constituted of three transducers Q1j, Q2j and Q3j that are discrete and do not exist on the same straight line. The position coordinates (xo, yo, zo) of the catheter tip part with the transducer 9 mounted thereon are calculated based on the distances R1j, R2j, and R3j between the respective transducers Q1j, Q2j and Q3j and the catheter tip part, the distances having been calculated using the above-described expression (2).

Hereinafter, a method for calculating the position coordinates (xo, yo, zo) of the catheter tip part with respect to the transducer groups Naj is shown using expressions (3) to (5). Where the position coordinates of the three transducers Q1j, Q2j, and Q3j constituting the transducer group Naj, respectively, are represented by (x1j, y1j, z1j), (x2j, y2j, z2j), and (x3j, y3j, z3j), the distances R1j, R2j, and R3j can be obtained by the following expression (3).

$R1j^2 = (xo-x1j)^2 + (yo-y1j)^2 + (zo-z1j)^2$ $R2j^2 = (xo-x2j)^2 + (yo-y2j)^2 + (zo-z2j)^2$ $R3j^2 = (xo-x3j)^2 + (y-y3j)^2 + (zo-z3j)^2 \quad (3)$ Then, by deforming the expression (3), the following simultaneous equations (expression (4)) regarding the relative position coordinates (xo, yo, zo) are obtained.

$R1j^2 - R2j^2 = 2(x2j-x1j)xo + (x1j^2 - x2j^2)$ $2(y2j-y1j)yo + (y1j^2 - y2j^2)$ $2(z2j-z1j)zo + (z1j^2 - z2j^2)$ $R2j^2 - R3j^2 = 2(x3j-x2)xo + (x2j^2 - x3j^2)$ $2(y3j-y2j)yo + (y2j^2 - y3j^2)$ $2(z3j-z2j)zo + (z2j^2 - z3j^2)$ $R3j^2 - R1j^2 = 2(x1j-x3j)xo + (x3j^2 - x1j^2)$ $2(y1j-y3j)yo + (y3j^2 - y1j^2)$ $2(z1j-z3j)zo + (z3j^2 - z1j^2) \quad (4)$ That is, the relative position coordinates (xo, yo, zo) of the catheter tip part with respect to the transducer groups Naj can be calculated using the following matrix (expression (5)), where $[A]^{-1}$ shows an inverse matrix of $[A]$.

$$[A]\begin{bmatrix} xo \\ yo \\ zo \end{bmatrix} = [B] \quad (5)$$

-continued $$\begin{bmatrix} xo \\ yo \\ zo \end{bmatrix} = [A]^{-1}[B]$$

$$[A] = \begin{bmatrix} 2(x2j-x1j) & 2(y2j-y1j) & 2(z2j-z1j) \\ 2(x3j-x2j) & 2(y3j-y2j) & 2(z3j-z2j) \\ 2(x1j-x3j) & 2(y1j-y3j) & 2(z1j-z3j) \end{bmatrix}$$

$$[B] = \begin{bmatrix} R1j^2 - R2j^2 - (x1j^2 - x2j^2) - (y1j^2 - y2j^2) - (z1j^2 - z2j^2) \\ R2j^2 - R3j^2 - (x2j^2 - x3j^2) - (y2j^2 - y3j^2) - (z2j^2 - z3j^2) \\ R3j^2 - R1j^2 - (x3j^2 - x1j^2) - (y3j^2 - y1j^2) - (z3j^2 - z1j^2) \end{bmatrix}$$

Here, letting the relative position coordinates (xo, yo, zo) of the transducer 9, obtained by using the transducer groups Naj be (xo(j), yo(j), zo(j)), the relative position coordinates (x, y, z) of the catheter tip part with respect to the ultrasonic probe 3 can be obtained by applying an averaging process to the relative position coordinates (xo(j), yo(j), zo(j)) (j=1 to J) with respect to the transducer groups Naj (j=1 to J) based on the following expression (6).

$$x = \frac{\sum_{j=1}^{J} xo(j)}{J} \quad y = \frac{\sum_{j=1}^{J} yo(j)}{J} \quad z = \frac{\sum_{j=1}^{J} zo(j)}{J} \tag{6}$$

Referring back to FIG. 1, the display unit 13 includes a display data generation circuit, a conversion circuit, and a monitor (none of which is shown). Based on the position coordinates (x, y, z) of the catheter tip part detected by the position detection part 12, the display data generation circuit superimposes position information (marker) showing the catheter tip part on a display of three-dimensional image data generated in the image data generation unit 5, and further generates display data by adding ancillary information such as object information to the image data. The conversion circuit applies a D/A (digital-to-analog) conversion and a display format conversion to the display data generated by the display data generation circuit, and displays it in real time on the monitor.

The input unit 14 includes input devices such as a display panel, a keyboard, a trackball, and a mouse provided on an operation panel. The input unit 14 performs the input of object information; the setting of the repetition period Tm in frequency modulation, the frequency shift width Δf in frequency modulation, and the center frequency f1 for the generation of an FMCW; the setting of the center frequency f1 and the bandwidth BW1 with respect to the BPF 111; the setting of the center frequency f2 and the bandwidth BW2 with respect to the BPF 221; the selection of image data acquisition mode, the setting of acquisition conditions or display conditions for image data; and further the input of various command signals.

The system control unit 15 includes a CPU (Central Processing Unit) and a storage circuit (neither of which is shown), and input/setting/selection information supplied from the input unit 14 is stored in the storage circuit. Based on these pieces of information, the CPU exerts general control over all the above-described units, and performs a display of three-dimensional image data on which the position information on the catheter tip part is superimposed. Especially, the CPU controls the delayed time in each of the transmission delay circuit 212 in the transmission unit 21 and the reception delay circuit 223 in the reception unit 22, each shown in FIG. 2, and performs a three-dimensional scan by ultrasonic waves with respect to the pertinent object.

(Procedure for Displaying Positional Information of the Catheter Tip Part)

Next, the displaying procedure of the position information on the catheter tip part in the embodiment will be described with reference to a flowchart in FIG. 8.

Prior to the acquisition of three-dimensional image data regarding the object, an operator of the ultrasonic diagnostic apparatus 100 inputs object information such as an object name and an object ID into the apparatus, and performs the selection of volume data generation mode or three-dimensional image data generation mode, and the setting of acquisition conditions for the volume data or the three-dimensional image data, with use of the input unit 14. The operator further performs the setting of the repetition period Tm in frequency modulation, and the frequency shift width Δf in frequency modulation, and the center frequency f1 for the generation of an FMCW; the setting of the center frequency f1 and the bandwidth BW1 with respect to the BPF 111; and the setting of the center frequency f2 and the bandwidth BW2 with respect to the BPF 221, with use of the input unit 14. Meanwhile, in this embodiment, the description is made of the case where "B-mode volume data" is selected as a volume data generation mode and "volume rendering image data" is selected as a three-dimensional image data generation mode, but these selections are not restrictive. The above-described input information, selection information, and setting information inputted through the input unit 14 are stored in the storage circuit in the system control unit 15 (step S1 in FIG. 8).

Figure 8:
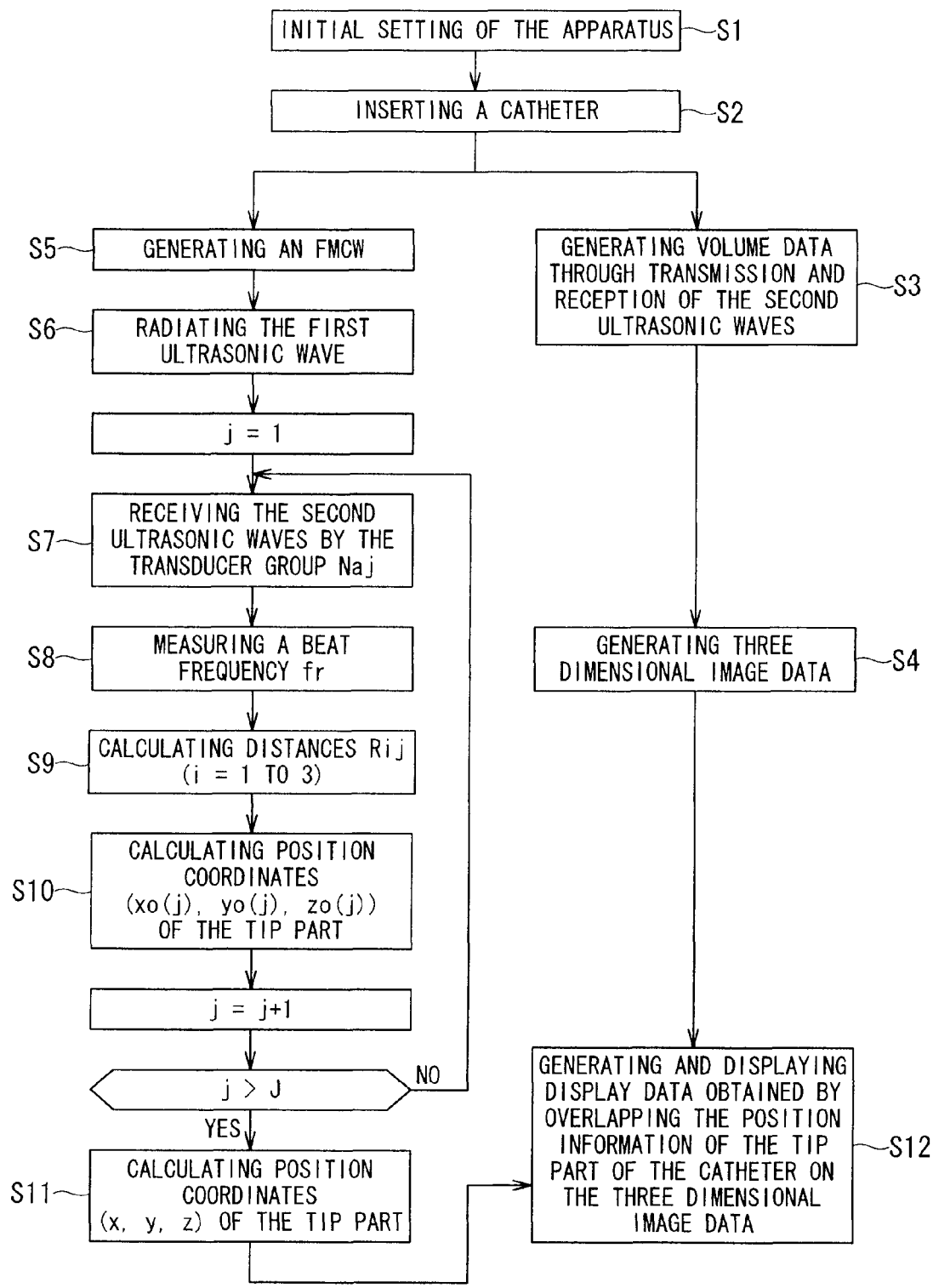
FIG. 8 is a flowchart showing a procedure for displaying position information of a tip part of a catheter according to the embodiment.

Upon completion of the above-described initial setting, the operator inserts a catheter 91 with a minute transducer 9 mounted on the tip part thereof into the body of the object (step S2 in FIG. 8). Then, with the ultrasonic probe 3 brought into contact with the body surface of the object, a three-dimensional image data acquisition start command is inputted by the input unit 14 into the apparatus 100. When this command signal is supplied to the system control unit 15, the system control unit 15 starts the generation of three-dimensional image data by the transmission/reception of the second ultrasonic waves having the center frequency f2 and the bandwidth BW2.

In generating the three-dimensional image data, the rate pulse generator 211 of the transmission unit 21, shown in FIG. 2 generates rate pulses in accordance with a control signal supplied from the system control unit 15, and provides them to the transmission delay circuit 212. The transmission delay circuit 212 provides the rate pulses with delayed times for converging the second ultrasonic waves to a predetermined depth to obtain a small beam width in the transmission of the second ultrasonic waves, and delayed times for transmitting the above-described second ultrasonic waves in an original transmission/reception direction (θ1, φ1), and supplies this rate pulses to the N channel drive circuit 213. Then, the drive circuit 213 generates drive signals having predetermined delayed times based on the rate pulses supplied from the transmission delay circuit 212, and supplies these drive signals to N transducers two-dimensionally arranged in the ultrasonic probe 3 to thereby radiate the second ultrasonic waves into the object body.

Some of the radiated second ultrasonic waves reflect on boundary surfaces between organs, or tissues having mutually different acoustic impedance, and after having been received by the above-described transducers, they are converted into N channel electric reception signals. Then, the N channel reception signals due to the second ultrasonic waves are bandwidth-limited by the BPF 221 in the reception unit 22, and converted into digital signals by the A/D converter 222. Thereafter, in the reception delay circuit 223, the N channel reception signals due to the second ultrasonic waves are provided with delayed times for converging the second ultrasonic waves from the predetermined depth and delayed times for setting a high reception directivity with respect to the above-described second ultrasonic waves from the transmission/reception direction ($\theta 1$, $\phi 1$), and the N channel reception signals are subjected to phasing/adding by the adder 224.

In the reception signal processing part 41 of the volume data generation unit 4 which has been supplied with the reception signal after phasing/adding, the envelope detector 411 and the logarithmic converter 412, respectively, apply envelope detection and logarithm conversion to the reception signal to generate B-mode data, and store it in the data storage 42.

Upon completion of the generation and storage of the B-mode data on the transmission/reception direction ($\theta 1$, $\phi 1$), ultrasonic waves are transmitted/received using the same procedure, in transmission/reception directions ($\theta 1$, $\phi 2$ to $\phi Q$) set to $\phi q = \phi 1 + (q-1) \Delta \phi$; (q=2 to Q) in which the transmission/reception direction is renewed by $\Delta \phi$ in the $\phi$ direction. At this time, the system control unit 15 renews, by control signals thereof, the delay time used in each of the transmission delay circuit 212 and the drive circuit 223, relating to the above-described transmission/reception directions.

Upon completing the ultrasonic wave transmission/reception in the transmission/reception directions ($\theta 1$, $\phi 1$ to $\phi Q$)) using the above-described procedure, the transmission/reception direction is set to $\theta p = \theta 1 + (p-1) \Delta \theta$; (p=2 to P) in which the transmission/reception direction is renewed by $\Delta \theta$ in the $\theta$ direction, and the above-described ultrasonic wave transmission/reception in the directions of $\phi 1$ to $\phi Q$ is repeated with respect to each of the transmission/reception directions of $\theta 2$ to $\theta P$, whereby a three-dimensional scan with respect to the object is performed. The B-mode data obtained regarding each of the transmission/reception directions are successively stored in the data storage 42, relating to the above-described transmission/reception directions, to thereby generate volume data (step S3 in FIG. 8).

Next, the opacity/tone setting unit in the image data generation unit 5 sets, in units of voxel, opacities and tones based on voxel values of the volume data read from the data storage 42 in the volume data generation unit 4. On the other hand, the rendering processing unit in the image data generation unit 5 rendering-processes the volume data based on information on the opacities and the tones set by the above-described opacity/tone setting unit to generate three-dimensional image data (step S4 in FIG. 8).

The saw-tooth wave generation circuit in the FMCW generation unit 7 generates a saw-tooth wave based on the repetition period Tm in frequency modulation, frequency shift width $\Delta f$ in frequency modulation, and the center frequency f1 of an FMCW that are each supplied from the system control unit 15. The VCO circuit generates an FMCW of which the frequency continuously changes at the period Tm based on the saw-tooth wave (step S5 in FIG. 8). The FMCW drive unit 8 amplifies the FMCW supplied from the FMCW generation unit 7 into a predetermined amplitude to generate an FMCW drive signal, and drives the transducer 9 mounted on the tip part of the catheter 91 to thereby radiate the first ultrasonic wave (step S6 in FIG. 8).

Next, the transducer group selection unit 10 selects transducer group Na1 to receive the first ultrasonic wave radiated by the transducer 9, from among the plurality of transducers two-dimensionally arranged in the ultrasonic probe 3, and a reception signal due to the first ultrasonic wave, received by each of the three transducers Q11, Q21, and Q31 in the transducer group Na1 is supplied to the beat frequency measuring unit 11, together with the above-described simultaneously received reception signal due to the second ultrasonic waves (step S7 in FIG. 8).

The BPF 111 in the beat frequency measuring unit 11 extracts the reception signal component due to the first ultrasonic wave out of the reception signals obtained from the transducer group Na1. The mixer 112 multiplies the reception signal due to the first ultrasonic wave, outputted from the BPF 111 by the FMCW supplied from the FMCW generation unit 7, and generates a reception signal with a sum frequency and a reception signal with a difference frequency (beat frequency) fr. Then, LPF 113 applies a filtering process to the reception signals outputted by the mixer 112 and extracts a reception signal with the beat frequency fr, and the frequency counter 114 measures the beat frequency fr of the reception signal supplied from the LPF 113 in a predetermined time period (step S8 in FIG. 8).

Next, the distance calculation unit 121 in the position detection part 12 calculates the distances R11, R21, and R31, respectively, from the transducers Q11, Q21, and Q31 of the transducer group Na1 to the transducer 9, by substituting the beat frequency fr measured by the frequency counter 114 into the above-described expression (2) (step S9 in FIG. 8). Based on the obtained distances R11, R21, and R31, the position coordinate calculation unit 122 calculates the relative position coordinates (xo(1), yo(1), zo(1)) of the catheter tip part with respect to the transducer group Na1 (step S10 in FIG. 8).

Upon completing the measurement of the position coordinates (xo(1), yo(1), zo(1)) of the catheter tip part, using the transducer group Na1, the transducer group selection unit 10 successively selects transducers Q1j, Q2j, and Q3j (j=2 to J) constituting the transducer groups Naj (j=2 to J), and the beat frequency measuring unit 11 measures the beat frequency fr of a reception signal due to the first ultrasonic wave, obtained here. Then, the position detection part 12 substitutes the measured beat frequency fr into the expression (2) to calculate distances Rij (i=1 to 3, j=2 to J). Furthermore, using the same procedure as that in the case where the transducer group Na1 was selected, the position detection part 12 calculates the position coordinates (xo(j), yo(j), zo(j)) (j=2 to J) of the catheter tip part with respect to each of the transducer groups Naj (j=2 to J) (steps S7 to S10 in FIG. 8).

Next, the average value calculation unit 123 in the position detection part 12 adds and averages the calculated position coordinates (xo(j), yo(j), zo(j)) (j=1 to J) based on the expression (6), to thereby calculate relative position coordinates (x, y, z) of the catheter tip part with respect to the ultrasonic probe 3 (step S11 in FIG. 8).

The display unit 13 superimposes the position information (marker) showing the catheter tip part, generated based on the above-described position coordinates (x, y, z) on three-dimensional image data generated in real time by the image data generation unit 5, and displays display data generated with adding ancillary information such as object information, on the display unit 13 (step S12 in FIG. 8).

According to the above-described embodiment of the present invention, since the distance between the transducer at the catheter tip part and each transducer in the ultrasonic probe is measured by measuring the beat frequency obtained by multiplying a reception signal due to the first ultrasonic wave by an FMCW, it is possible to perform an accurate distance measurement without being much influenced by the waveform deterioration due to the ultrasonic attenuation in body tissues or the waveform changes due to the directivity characteristics of transducers for transmission.

Furthermore, since the center frequency f1 of the first ultrasonic wave as an FMCW can be set to a lower value than the center frequency f2 of the second ultrasonic wave used for the generation of three-dimensional image data, the influence of the ultrasonic attenuation in body tissues can be suppressed. Moreover, since the bandwidth of the first ultrasonic wave as the FMCW can be set to a narrower width compared with that of the second ultrasonic wave, the influence of noises can be reduced.

Furthermore, according to the above-described embodiment, a plurality of transducer groups is selected from among a plurality of transducers two-dimensionally arranged in the ultrasonic probe, and the position coordinates of the catheter tip part, obtained using each of these transducer groups are subjected to an averaging process, to thereby calculate the position coordinates of the catheter tip part with respect to the ultrasonic probe. Therefore, the influence of uneven ultrasonic attenuation or sound speed in body tissues can be cancelled out. This allows the position coordinates of the catheter tip part to be measured with accuracy and stability.

Moreover, in this embodiment, since the center frequency and the bandwidth of each of the first ultrasonic wave and the second ultrasonic wave are set so that the frequency component of the first ultrasonic wave and that of the second ultrasonic wave can be separated, the measurement of the position coordinates of the catheter tip part and the generation of three-dimensional image data can be concurrently performed. This allows the measurement of the position coordinates of the catheter tip part to be continuously performed without reducing the frame frequency (number of pieces of image data displayable per unit time) in the display of three-dimensional image data.

For the above-described reason, according to this embodiment, since the catheter tip part inserted into the body of the object can be accurately and stably monitored on the three-dimensional image data, the stability in diagnosis/treatment using a catheter is ensured, and also the efficiency of the diagnosis/treatment is significantly enhanced.

Having described the embodiment of the present invention, the present invention is not limited to the above-described embodiment, and various modifications may be made therein. For example, in the above-described embodiment, the case has been described in which one transducer group is constituted by three transducers that are discretely disposed in the ultrasonic probe 3, but the transducer group may be constituted by four transducers or more.

In addition, in the position detection part 12 in the above-described embodiment, the case has been explained in which the relative position coordinates (x, y, z) of the catheter tip part with respect to the ultrasonic probe 3 are calculated by adding and averaging the J sets of position coordinates (xo(j), yo(j), zo(j)) (j=1 to J) calculated through the plurality of transducer groups Naj (j=1 to J), but the above-described position coordinates (x, y, z) can also be obtained by calculating the center value or the barycenter value of a histogram based on the above-described position coordinates (xo(j), yo(j), zo(j)) (j=1 to J).

Further, though a case where volume rendering image data is generated as three-dimensional image data based on B mode data is described in the above-mentioned embodiment, volume rendering image data based on other ultrasonic data such as color Doppler data and/or other three-dimensional image data such as surface rendering image data instead of volume rendering image data may be generated, as already described.

Further, a case where three-dimensionally positional information of the catheter tip part is overlapped on three-dimensional image data generated by using the ultrasonic probe 3 having two-dimensionally arrayed transducers to be displayed is described in the above-mentioned embodiment. However, embodiments are not limited to the above-mentioned case. For example, two-dimensionally positional information of the catheter tip part may be overlapped onto two-dimensional image data generated by using an ultrasonic probe having one-dimensionally arrayed transducers to be displayed.

Further, though a position of the tip part of the catheter 91 is calculated by arranging a single transducer 9 on the tip part of the catheter 91 and assuming a position of the transducer 9 as the position of the tip part of the catheter 91 in the above-mentioned embodiment, plural transducers 9 may be provided with the tip part of the catheter 91. When plural transducers 9 are provided with the tip part of the catheter 91, a position of the tip part of the catheter 91 can be calculated more precisely by the use of geometrical positional relationship between the transducers 9.

Figure 9:
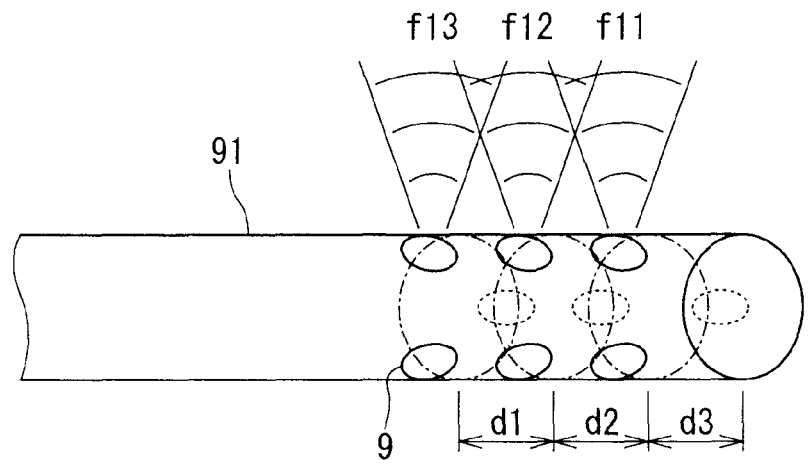
FIG. 9 is a structural diagram showing an example of plural transducers provided with a tip part of a catheter.
Figure 10:
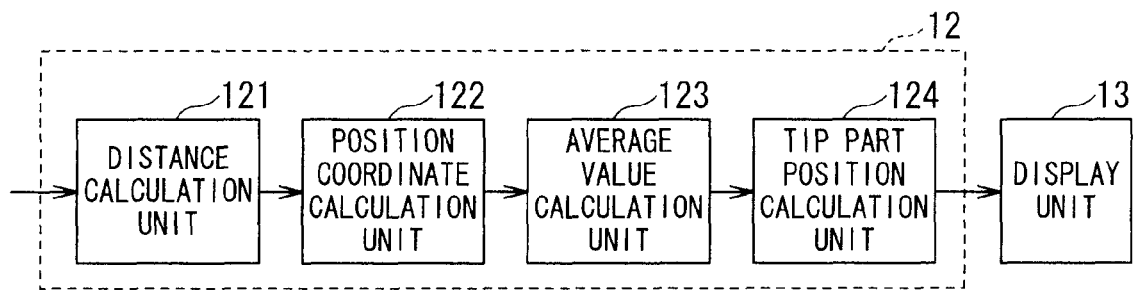
FIG. 10 is a block diagram showing an example configuration of the position detection part in case of providing plural transducers with a tip part of a catheter.

FIG. 9 is a structural diagram showing an example of plural transducers 9 provided with a tip part of a catheter 91. FIG. 10 is a block diagram showing an example configuration of the position detection part 12 in case of providing plural transducers 9 with a tip part of a catheter 91.

As shown in FIG. 9, plural transducers 9 can be mounted at the tip part of the catheter 91. According to an example shown in FIG. 9, nine transducers 9 are mounted at the tip part of the catheter 91. That is, three transducers 9 are mounted at approximate even intervals on an outer circumference which is a distance d1 from the tip of the catheter 91. Three transducers 9 are mounted at approximate even intervals on an outer circumference which is a distance d2 from three transducers 9 mentioned above in the length direction of the catheter 91. Further, three transducers 9 are mounted at approximate even intervals on an outer circumference which is a distance d3 from three transducers 9 mentioned above in the length direction of the catheter 91. The positions of three transducers 9 in the length direction of the catheter 91 can be determined arbitrarily, according to an example shown in FIG. 9, they are arranged collinearly.

Thus, when plural transducers 9 are mounted at the different positions on the catheter 91, the position coordinates of each transducer 9 can be calculated at the position detection part 12 under the method mentioned above after the first ultrasonic wave transmitted from each transducer 9 is received with the ultrasonic probe 3.

In this case, it is preferable to change a center frequency to identify a transducer 9 transmitting each first ultrasonic wave. According to an example shown in FIG. 9, the first ultrasonic waves are transmitted at a center frequency f11 from the three transducers 9 arranged at the positions which are distance d1 from the tip of the catheter 91, the first ultrasonic waves are transmitted at a center frequency f12 from the three transducers 9 arranged at the positions which are distance d1+d2 from the tip of the catheter 91, and the first ultrasonic waves are transmitted at a center frequency f13 from the three transducers 9 arranged at the positions which are distance d1+d2+d3 from the tip of the catheter 91.

The frequency band of the first ultrasonic wave having each of the center frequencies f11, f12, f13 is set without overlapping that of the second ultrasonic wave as mentioned above. Further, when the band of the first ultrasonic wave having the center frequency f11, that of the first ultrasonic wave having the center frequency f12 and that of the first ultrasonic wave having the center frequency f13 are set without overlap mutually, it is possible to identify which transducer 9 transmits a first ultrasonic wave more satisfactory. Note that, the first ultrasonic waves may be transmitted at the mutually different center frequencies respectively from plural transducers 9 which are at different positions in the direction of the outer circumference in addition to or instead of the length direction of the catheter 91.

Then, since relative positional relationship between the respective transducers 9 is known, a position coordinate of the tip of the catheter 91 can be calculated geometrically using each position coordinates of at least two transducers which are at mutually different positions in the length of the catheter 91. On the other hand, since the diameter of the catheter 91 is known, the position coordinates of the central axis can be calculated geometrically using each position coordinate of at least two transducers 9 which are at mutually different positions in the direction of outer circumference of the catheter 91. Note that, it is preferable on accuracy that three and above transducers 9 are mounted at mutually different positions in the direction of the outer circumference of the catheter 91 in the case of calculating the position coordinates of the center axis of the catheter 91.

Further, when the number of transducers 9 arranged at mutually different positions in the length direction or in the outer circumference direction of the catheter 91 is increased and the position coordinates of the tip and the central axis of the catheter 91 are calculated with averaging processing, accuracy of calculation can be improved. Therefore, it is favorable on accuracy to set the distances d1, d2, and d3 longer. However, it is necessary to arrange the respective transducers 9 at positions where the first ultrasonic waves can be receive with the ultrasonic probe 3. Consequently, as a concrete example, the distances d1, d2, and d3 can be determined to d1=d2=d3=approximate 1 mm. According to the calculation of position coordinates of the tip and the central axis of the catheter 91 based on each position coordinates of plural transducers 9, it is possible to calculate with approximate dozens of μm accuracy.

In the above-mentioned case, the tip part position calculation unit 124 which has functions to calculate the position coordinates of the tip and the central axis of the catheter 91 geometrically based on each position coordinates of plural transducers 9 described above and to perform averaging processing is set subsequently to the average value calculation unit 123. That is, the tip part position calculation unit 124 calculates the position coordinates of the tip and the central axis of the catheter 91 using the position coordinates of each of the transducers 9 obtained from the average value calculation unit 123 and gives the calculation result to the display unit 13. This allows superimposed display of three-dimensional ultrasonic image data and position information which shows the tip part of the catheter 91 on the display unit 13.

Note that, the aperture of each transducer 9 is determined to be a size so that the first ultrasonic wave can be received with the ultrasonic probe 3 under the condition that the first ultrasonic wave can be considered as an omnidirectional spherical wave enough. Specifically, as mentioned above, the aperture of each transducer 9 is set to be smaller than the wavelength of the first ultrasonic wave having 0.8 MHz center frequency.

Since the first ultrasonic wave transmitted from each transducer 9 respectively is omnidirectional spherical wave, there is possibility that the first ultrasonic wave does not be transmitted toward the side of the ultrasonic probe 3 and can't be received with sufficient accuracy depending on a direction of the catheter 91.

Therefore, when plural transducers 9 are arranged at mutually different positions in the direction of the outer circumference of the catheter 91, it is possible not only to calculate for the position coordinates of the center axis of the catheter 91 as mentioned above but to transmit the first ultrasonic waves to plural directions. Therefore, even though the ultrasonic probe 3 can't receive the first ultrasonic waves from a part of transducers 9 appropriately depending on the direction of the catheter 91, since the first ultrasonic waves from other transducers 9 are toward to the ultrasonic probe 3, the first ultrasonic waves can be received with stability independent of the direction of the catheter 91.

What is claimed is:

1. An ultrasonic diagnostic apparatus comprising:
   plural ultrasonic transducers arrayed two-dimensionally for transmitting and receiving ultrasonic waves to and from an object;
   a catheter signal detection unit configured to acquire a reception signal of a frequency modulated continuous wave from reception signals from at least three of said plural ultrasonic transducers, the frequency modulated continuous wave being transmitted from a catheter inserted in the object;
   a position detection unit configured to detect a position of the catheter based on the acquired reception signal of the frequency modulated continuous wave;
   a transmission-and-reception unit configured to transmit and receive pulse ultrasonic waves through said plural ultrasonic transducers, the pulse ultrasonic waves each having a frequency band different from that of the frequency modulated continuous wave;
   a signal separation unit configured to separate a first component resulting from the frequency modulated continuous wave from a second component resulting from the pulse ultrasonic waves, the first and second components being included in reception signals obtained by said transmission-and-reception unit; and
   an ultrasonic image generation unit configured to generate an ultrasonic image using the second component obtained by said signal separation unit.

2. An ultrasonic diagnostic apparatus of claim 1,
   wherein said position detection unit is configured to measure a beat frequency of the reception signal of the frequency modulated continuous wave to detect the position of the catheter based on the obtained beat frequency.

3. An ultrasonic diagnostic apparatus of claim 1,
   wherein said catheter signal detection unit is configured to acquire the first component obtained by said signal separation unit as the reception signal of the frequency modulated continuous wave.

4. An ultrasonic diagnostic apparatus of claim 1, further comprising:
   a transducer group selection unit configured to select at least three ultrasonic transducers from said plural ultrasonic transducers, the three ultrasonic transducers being for acquiring the reception signal of the frequency modulated continuous wave.

5. An ultrasonic diagnostic apparatus of claim 1, further comprising:
   a transducer group selection unit configured to select plural transducer groups each having at least three ultrasonic transducers from said plural ultrasonic transducers, the three ultrasonic transducers being for acquiring the reception signal of the frequency modulated continuous wave,
   wherein said position detection unit is configured to measure a beat frequency of the reception signal of the frequency modulated continuous wave, calculate respective distances between the catheter and the three ultrasonic transducers of each of the plural transducer groups based on the obtained beat frequency, and perform average processing to positions of the catheter respectively obtained for the plural transducer groups based on the calculated respective distances.

6. An ultrasonic diagnostic apparatus of claim 1, further comprising:
a transducer group selection unit configured to select at least three discrete ultrasonic transducers from said plural ultrasonic transducers, the three ultrasonic transducers being for acquiring the reception signal of the frequency modulated continuous wave.

7. An ultrasonic diagnostic apparatus of claim 3, wherein said transmission-and-reception unit is configured to transmit and receive the pulse ultrasonic waves having a center frequency higher than that of the frequency modulated continuous wave.

8. An ultrasonic diagnostic apparatus of claim 3, wherein said transmission-and-reception unit is configured to transmit and receive the pulse ultrasonic waves so as to make a center frequency of the frequency modulated continuous wave outside a signal band of the pulse ultrasonic waves.

9. An ultrasonic diagnostic apparatus of claim 1, wherein said catheter signal detection unit is configured to acquire the reception signal of the frequency modulated continuous wave from reception signals from plural transducer groups each having at least three ultrasonic transducers, and
said position detection unit includes:
a beat frequency measuring unit configured to measure a beat frequency of the reception signal of the frequency modulated continuous wave;
a distance calculation unit configured to calculate respective distances between the catheter and the three ultrasonic transducers of each of the plural transducer groups based on the beat frequency measured by said beat frequency measuring unit;
a first position calculation unit configured to calculate respective positions of the catheter corresponding to the plural transducer groups based on the respective distances; and
a second position calculation unit configured to calculate a relative position of the catheter to an ultrasonic probe having said plural ultrasonic transducers by average processing to the respective positions of the catheter corresponding to the plural transducer groups.

10. An ultrasonic diagnostic apparatus of claim 1, wherein said position detection unit is configured to measure a beat frequency of the reception signal of the frequency modulated continuous wave by zero cross count to detect the position of the catheter based on the obtained beat frequency.

11. An ultrasonic diagnostic apparatus of claim 1, wherein said catheter signal detection unit is configured to acquire reception signals of frequency modulated continuous waves respectively transmitted from plural ultrasonic transducers provided with the catheter.

12. An ultrasonic diagnostic apparatus of claim 1, wherein said catheter signal detection unit is configured to acquire reception signals of frequency modulated continuous waves respectively transmitted from plural ultrasonic transducers provided with the catheter, and
said position detection unit is configured to detect the position of the catheter based on the reception signals of the frequency modulated continuous waves.

13. A catheter tip part detection method comprising:
acquiring a reception signal of a frequency modulated continuous wave from reception signals from at least three of two-dimensionally arrayed plural ultrasonic transducers, the frequency modulated continuous wave being transmitted from a catheter inserted in an object;
detecting a position of the catheter based on the acquired reception signal of the frequency modulated continuous wave;
transmitting and receiving pulse ultrasonic waves through the plural ultrasonic transducers, the pulse ultrasonic waves each having a frequency band different from that of the frequency modulated continuous wave;
separating a first component resulting from the frequency modulated continuous wave from a second component resulting from the pulse ultrasonic waves, the first and second components being included in reception signals obtained by the plural ultrasonic transducers; and
generating an ultrasonic image using the separated second component.

14. A catheter tip part detection method of claim 13, wherein a beat frequency of the reception signal of the frequency modulated continuous wave is measured to detect the position of the catheter.

15. A catheter tip part detection method of claim 13, wherein the separated first component is acquired as the reception signal of the frequency modulated continuous wave.

16. A catheter tip part detection method of claim 13, further comprising:
selecting at least three ultrasonic transducers from the plural ultrasonic transducers, the three ultrasonic transducers being for acquiring the reception signal of the frequency modulated continuous wave.

17. A catheter tip part detection method of claim 13, further comprising:
selecting plural transducer groups each having at least three ultrasonic transducers from the plural ultrasonic transducers, the three ultrasonic transducers being for acquiring the reception signal of the frequency modulated continuous wave,
wherein a beat frequency of the reception signal of the frequency modulated continuous wave is measured, respective distances between the catheter and the three ultrasonic transducers of each of the plural transducer groups are calculated based on the obtained beat frequency, and average processing is performed to positions of the catheter respectively obtained for the plural transducer groups based on the calculated respective distances.

18. A catheter tip part detection method of claim 13, further comprising:
selecting at least three discrete ultrasonic transducers from the plural ultrasonic transducers, the three ultrasonic transducers being for acquiring the reception signal of the frequency modulated continuous wave.

19. A catheter tip part detection method of claim 15, wherein the pulse ultrasonic waves having a center frequency higher than that of the frequency modulated continuous wave are transmitted and received.

20. A catheter tip part detection method of claim 15, wherein the pulse ultrasonic waves are transmitted and received so as to make a center frequency of the frequency modulated continuous wave outside a signal band of the pulse ultrasonic waves.

21. A catheter tip part detection method of claim 13,
wherein the reception signal of the frequency modulated continuous wave is acquired from reception signals from plural transducer groups each having at least three ultrasonic transducers, and
detecting the position of the catheter includes:
measuring a beat frequency of the reception signal of the frequency modulated continuous wave;
calculating respective distances between the catheter and the three ultrasonic transducers of each of the plural transducer groups based on the measured beat frequency;
calculating respective positions of the catheter corresponding to the plural transducer groups based on the respective distances; and
calculating a relative position of the catheter to an ultrasonic probe having the plural ultrasonic transducers by average processing to the respective positions of the catheter corresponding to the plural transducer groups.

22. A catheter tip part detection method of claim 13,
wherein a beat frequency of the reception signal of the frequency modulated continuous wave is measured by zero cross count to detect the position of the catheter.

23. A catheter tip part detection method of claim 13,
wherein reception signals of frequency modulated continuous waves respectively transmitted from plural ultrasonic transducers provided with the catheter are acquired.

24. A catheter tip part detection method of claim 13,
wherein reception signals of frequency modulated continuous waves respectively transmitted from plural ultrasonic transducers provided with the catheter are acquired, and
the position of the catheter is detected based on the reception signals of the frequency modulated continuous waves.

* * * * *